(12) United States Patent
Huang et al.

(10) Patent No.: US 9,678,014 B2
(45) Date of Patent: Jun. 13, 2017

(54) CAPILLARY FLOW PLASMONIC SENSOR

(71) Applicant: IMEC VZW, Leuven (BE)

(72) Inventors: Chengjun Huang, Leuven (BE);
Liesbet Lagae, Leuven (BE)

(73) Assignee: IMEC VZW, Leuven (BE)

( * ) Notice: Subject to any disclaimer, the term of this patent is extended or adjusted under 35 U.S.C. 154(b) by 72 days.

(21) Appl. No.: 14/554,429

(22) Filed: Nov. 26, 2014

(65) Prior Publication Data

US 2015/0153283 A1    Jun. 4, 2015

(30) Foreign Application Priority Data

Nov. 29, 2013   (EP) .................................. 13195066

(51) Int. Cl.
*G01N 21/65* (2006.01)
*G01N 33/543* (2006.01)
(Continued)

(52) U.S. Cl.
CPC ........ *G01N 21/658* (2013.01); *B01L 3/50273* (2013.01); *G01N 21/554* (2013.01);
(Continued)

(58) Field of Classification Search
CPC .............. G01N 21/658; G01N 21/554; G01N 33/54386; G01N 33/54306; B01L 3/50273
See application file for complete search history.

(56) References Cited

U.S. PATENT DOCUMENTS 6,454,924 B2 * 9/2002 Jedrzejewski ....... B01J 19/0046
204/193
2007/0059488 A1    3/2007 Aizenberg et al.
(Continued)

FOREIGN PATENT DOCUMENTS

FR    2 979 704 A1    3/2013
WO    2006/138442 A2   12/2006
(Continued)

OTHER PUBLICATIONS

European Search Report, European Patent Application No. 13195066.9 dated Apr. 7, 2014.
(Continued)

*Primary Examiner* — Melanie Y Brown
(74) *Attorney, Agent, or Firm* — McDonnell Boehnen Hulbert & Berghoff LLP (57) ABSTRACT

In a first aspect, a micro-fluidic device is presented, comprising: a micro-fluidic channel having an inner surface; a sensing region inside the micro-fluidic channel configured for adsorbing at least one analyte, the sensing region comprising a plurality of pillars positioned along the length of the inner surface of the micro-fluidic channel wherein the plurality of pillars are configured for creating an electromagnetic field localization thereby making the sensing region suitable for sensing plasmonic or surface enhanced Raman signals when irradiated; characterized in that: the plurality of pillars are further configured for creating a capillary action in the micro-fluidic channel when a fluid sample is present in the micro-fluidic channel. In a second aspect, a multiplexed plasmonic microchip for detecting at least one analyte in a fluid sample is presented, comprising: a plurality of micro-fluidic devices as presented in the first aspect; a supply system for providing the fluid sample to the plurality of micro-fluidic devices. Further, a method for detecting analytes is presented using a device according the first or second aspect.

18 Claims, 7 Drawing Sheets

(51) Int. Cl.
 *G01N 21/552* (2014.01)
 *B01L 3/00* (2006.01)
(52) U.S. Cl.
 CPC . *G01N 33/54306* (2013.01); *G01N 33/54386* (2013.01); *B01L 2300/0636* (2013.01); *B01L 2300/0816* (2013.01); *B01L 2300/0864* (2013.01); *B01L 2400/0406* (2013.01); *B01L 2400/086* (2013.01)

(56) References Cited

U.S. PATENT DOCUMENTS

| | | | | |
|---|---|---|---|---|
| 2008/0223794 | A1* | 9/2008 | Yamamichi | B01J 20/28014 210/767 |
| 2009/0279085 | A1 | 11/2009 | Ebstein | |
| 2010/0307617 | A1* | 12/2010 | Miura | B01L 3/50273 137/565.01 |
| 2014/0186215 | A1* | 7/2014 | Shinta | G01N 21/554 422/69 |
| 2014/0209463 | A1* | 7/2014 | Gibson | B03C 5/005 204/547 |
| 2015/0253321 | A1* | 9/2015 | Chou | G01N 33/54366 435/5 |
| 2016/0107178 | A1* | 4/2016 | Velasquez-Garcia | B05B 1/14 239/3 |

FOREIGN PATENT DOCUMENTS

| | | |
|---|---|---|
| WO | 2008/101348 A1 | 8/2008 |
| WO | 2009/088408 A1 | 7/2009 |
| WO | 2012/172971 | * 12/2012 |

OTHER PUBLICATIONS

Liu, Gang et al., "Nanowell Surface Enhanced Raman Scattering Arrays Fabricated by Soft Lithography for Label-Free Biomolecular Detections in Integrated Microfluidics", Applied Physics Letters, American Institute of Physics, vol. 87, No. 7, Aug. 11, 2005, pp. 1-3.
Schmidt, Michael Stenbeck et al., "Towards Easily Reproducible Nano-Structured SERS Substrates", IEEE Sensors, Oct. 2009, pp. 1763-1767.
Pio, Michael S. et al., "Batch Fabrication of Nanopillars for Autonomous Nanofluidic SERS Arrays", Materials Research Society Symposium Proceedings, Materials Research Society, vol. 729, Apr. 1, 2002, pp. 179-184.

* cited by examiner

CAPILLARY FLOW PLASMONIC SENSOR

RELATED APPLICATION

This application claims priority to European application no. 13195066.9, filed Nov. 29, 2013, the disclosure of which is incorporated herein by reference in its entirety.

FIELD OF THE DISCLOSURE

The field of the disclosure is related to plasmonic sensors.

BACKGROUND TO THE DISCLOSURE

Surface Enhanced Raman Spectroscopy (SERS), surface plasmon resonance (SPR) and localized surface plasmon resonance (LSPR) measurement techniques are very sensitive techniques to measure small molecules, even at the single molecule level. SERS is a surface sensitive technique which results in the enhancement of Raman scattering by materials adsorbed or bound, i.e., in close contact with or in the vicinity of metal surfaces. In surface enhanced Raman scattering the local electromagnetic field is greatly enhanced at a metal surface. In Surface Plasmon Resonance, light interacts with a metal surface, giving rise to collective oscillations of electrons at the surface. The angle of reflection depends on the dielectric constant of the materials adsorbed on the surface of the metal film. LSPR is a phenomenon whereby light interacts with a nanostructure, giving rise to coherent localized plasmon oscillations with a resonant frequency that strongly depends on the composition, size, geometry, dielectric environment and separation distance of the nanostructure. SPR and LSPR have been used for chemical and biological sensing of molecules, proteins, DNA/RNA, viruses, microorganisms and cells. Both techniques are extremely useful for following binding kinetics and for real-time molecule detection.

The state of the art comprises two types of plasmonic or surface enhanced Raman sensing devices. A first type uses a sensing surface that is covered with a thin metal film such as gold or silver. The thin metal film is used for sensing purposes. A second type uses patterned metal structures or patterned structures that are coated with metal nanoparticles. These nanoparticles are used for sensing purposes. For example, Schmidt et al. ("Towards easily reproducible nano-structured SERS substrate", 2009 IEEE Sensors, Pages: 1763-7) describes a SERS substrate wherein pillars are coated with a thin metal film for enhancing the Raman effect.

To propagate a fluid sample through these devices, other MEMS components such as flow cells, fluidic channels or pumps are necessary. These components increase the size and cost of the device. As the total cost of these devices is high, they cannot be used as disposable devices.

SUMMARY OF THE DISCLOSURE

We recognized a need for a micro-fluidic plasmonic sensing device which overcomes at least some of the drawbacks described above.

In a first aspect of the disclosure a micro-fluidic device is presented, comprising a micro-fluidic channel having an inner surface; a sensing region inside the micro-fluidic channel configured for adsorbing at least one analyte, the sensing region comprising a plurality of pillars positioned along the length of the inner surface of the micro-fluidic channel wherein the plurality of pillars are configured for creating an electromagnetic field localization thereby making the sensing region suitable for sensing plasmonic or surface enhanced Raman signals when irradiated; wherein the plurality of pillars are further configured for creating a capillary action in the micro-fluidic channel when a fluid sample is present in the micro-fluidic channel. The sensing region of the micro-fluidic device also functions as a capillary pump. Hence, there is no need for an extra pump to propagate a fluid sample through the device. As an advantage, the micro-fluidic device is cheaper and more compact.

According to an embodiment of the disclosure, the sensing region is configured for adsorbing an analyte by containing a surface chemistry layer for binding at least one analyte. The surface chemistry layer binds analytes to the surface of the sensing region. Different surface chemistry layers may be used for detecting different analytes.

According to an embodiment of the disclosure, the plurality of pillars are configured for creating an electromagnetic field localization by having plasmonic nanoparticles or plasmonic nanostructures positioned on the surface of the plurality of pillars. Plasmonic nanoparticles or plasmonic nanostructures are positioned thereby creating an electromagnetic field localization when irradiated.

According to an embodiment of the disclosure, the plurality of pillars is configured for creating an electromagnetic field localization by having the plurality of pillars fabricated from a plasmonic material. The material of the plasmonic pillars itself allows creating an electromagnetic field localization when irradiated. As an advantage, a layer of a plasmonic material, nanoparticles or nanostructures do not need to be deposited on the pillars to create an electromagnetic field localization when irradiated. This makes the device easier to fabricate.

According to an embodiment of the disclosure, the plurality of pillars are configured for creating an electromagnetic field localization by having a coating of a plasmonic material. A layer of a plasmonic material is deposited on pillars and creates an electromagnetic field localization when irradiated.

According to an embodiment of the disclosure, the plurality of pillars are configured for creating a capillary action by having each pillar having a height and a diameter, wherein the spacing in between each pillars is adapted for creating the capillary action in the micro-fluidic channel. The diameter, height, and distance between the pillars create a capillary action in the micro-fluidic channel. As an advantage, a pump is not needed to propagate a fluid sample through the micro-fluidic device.

According to an embodiment of the disclosure, the micro-fluidic channel and the plurality of pillars are fabricated from silicon. Silicon is a material which allows the fabrication of high aspect ratio pillars which increases the surface area of the sensing region. Also, silicon is a material which may be processed using semiconductor processing techniques, e.g., CMOS compatible process steps. This makes the device cheaper and easier to fabricate. Further, silicon is an inert material which makes it ideal for biosensing applications.

According to an embodiment of the disclosure, the micro-fluidic channel and the plurality of pillars are at least partially fabricated from an optical transparent material. The optical transparent material allows light to travel through the material. As an advantage, a more efficient detection with a detector can be performed.

In a second aspect of the disclosure, a multiplexed plasmonic microchip for detecting at least one analyte in a fluid sample is presented, comprising: a plurality of micro-fluidic devices according to the first aspect of the disclosure; a supply system for providing a fluid sample to the plurality of micro-fluidic devices. The fluid sample may be distributed among the plurality of micro-fluidic devices wherein each micro-fluidic device may perform a detection on the fluid sample. As an advantage, detection may be done faster, more efficient and more sensitive.

According to an embodiment of the disclosure, different micro-fluidic devices are configured for adsorbing different analytes. Different micro-fluidic device are configured to detect different analytes. As an advantage, different analytes can be detected by the same multiplexed plasmonic microchip.

According to an embodiment of the disclosure, the multiplexed plasmonic microchip further comprises a transistor layer. The transistor layer allows electrical controlling of different electrical components in the multiplexed plasmonic microchip. The transistor layer may also comprise electrical components for biosensing purposes. As an advantage, the detection of analytes may be performed on-chip.

The micro-fluidic device according to the first aspect of the disclosure and the multiplexed plasmonic microchip according to the second aspect of the disclosure may be used for the real-time detection of at least one analyte. Thus, no labeling of the analyte must be done to perform the detection. As an advantage, detection can be done faster.

In a third aspect of the disclosure, a method for detecting at least one analyte in a fluid sample using the multiplexed plasmonic microchip described in the second aspect of the disclosure is presented, the method comprising: providing a fluid sample to the plurality of micro-fluidic devices using the supply system; irradiating the plurality of micro-fluidic devices and the fluid sample with a radiation source configured to perform LSPR or SERS; measuring surface plasmon resonance or Raman scattering from the plurality of irradiated micro-fluidic devices; and correlating the measured surface plasmonic resonance or Raman scattering to the presence or concentration of the at least one analyte in the fluid sample.

According to embodiments of the disclosure, the at least one analyte is a label-free analyte. As an advantage, no time consuming preparation steps, such as a labeling step, must be performed to detect the analyte. Also, detection can be performed faster.

DESCRIPTION OF THE DISCLOSURE

In embodiments of the disclosure where reference is made to a "label", this is referred to as a label which emits light on binding with, e.g., an antibody.

In embodiments of the disclosure where reference is made to a "labeled analytes", these are referred to as analytes or chemical components which have been treated to comprise a label which emits light on binding with e.g., an antibody.

In embodiments of the disclosure where reference is made to "LSPR", this is referred to as an abbreviation for localized surface plasmon resonance.

In embodiments of the disclosure where reference is made to "SERS", this is referred to as an abbreviation for surface enhanced Raman scattering.

In embodiments of the disclosure where reference is made to "analyte" or "analytes", this includes analytes of a biological nature.

In embodiment of the disclosure where reference is made to "real-time detection", this is referred to as detection of analytes in a fluid sample without performing preparation steps on the fluid sample prior to detection.

In embodiments of the disclosure where reference is made to "a plasmonic material", this refers to a material suitable for performing plasmonic or surface enhanced Raman experiments, for example suitable for performing LSPR or SERS. This material may be gold, silver, copper or any other material with similar properties.

Embodiments of the disclosure provide a very sensitive device for detecting analytes in a fluid sample without the need of additional preparation steps on the fluid sample, thereby enabling real-time detection of analytes in fluid sample.

Embodiments of the disclosure provide a lower cost and very sensitive sensing device which can be used as a disposable sensing device.

Embodiments of the disclosure provide a lower cost and sensitive sensing device which enables multiplexed or simultaneous detection of the same or different analytes in a fluid sample.

The disclosure provides a very sensitive, cheap and label-free detection technique and device for detecting analytes in a fluid sample.

Figure 1:
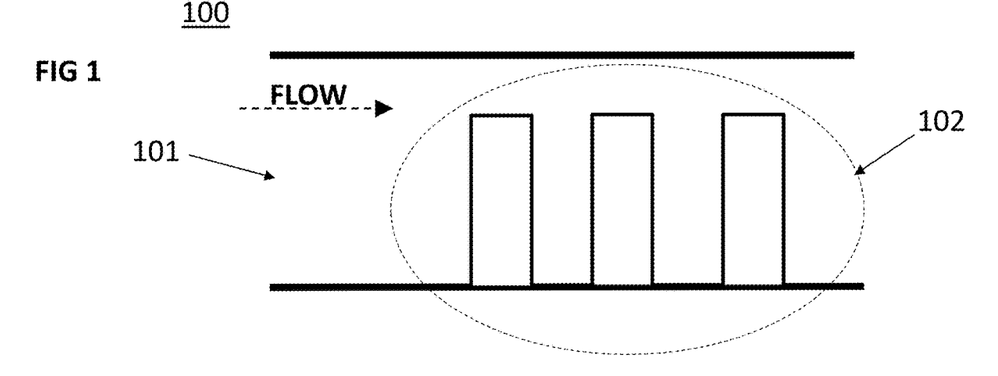
FIG. 1 illustrates an embodiment of the disclosure

In a first aspect of the disclosure, a micro-fluidic device 100 for sensing or detecting analytes is presented. The device 100 comprises: a micro-fluidic channel 101 having an inner surface; a sensing region present inside the micro-fluidic channel 101 and configured for adsorbing at least one analyte. The sensing region comprises a plurality of pillars 102 which are positioned along the length of the inner surface of the micro-fluidic channel 101. The plurality of pillars 102 are configured for creating an electromagnetic field localization thereby making the sensing region suitable for sensing plasmonic or surface enhanced Raman signals when being irradiated. The plurality of pillars 102 are further configured for creating a capillary action in the micro-fluidic channel 101 when a fluid is present in the micro-fluidic channel 101.

The micro-fluidic device 100 may comprise a substrate in which the micro-fluidic channel 101 is at least partly embedded . The micro-fluidic channel 101 may be an open or a closed micro-fluidic channel. The material of the substrate may be an inert material that does not interact with analytes in a fluid sample introduced in the micro-fluidic channel 101. For example, the material of the substrate should not interact with bio-fluids such as any fluid originating from the human body. The substrate material may be silicon. If the substrate material is a semiconductor material, standard lithographic techniques, e.g., CMOS compatible process steps, can be used to fabricate the micro-fluidic device 100. This allows miniaturization, compactness, and reduced cost of the micro-fluidic device 100.

Inside the micro-fluidic channel 101, a sensing region is present. The sensing region is configured to adsorb selected analytes and to detect the selected analytes adsorbed on the sensing region. The configuration of the sensing region comprises the presence of a surface chemistry layer comprising receptors for binding the selected analyte. The surface chemistry layer may be formed on the sensing region. The sensing region comprises a plurality of pillars 102. The pillars 102 may be micro-pillars or nano-pillars. The pillars 102 are positioned along the length of the inner surface of the micro-fluidic channel 101. The pillars 102 are configured for creating an electromagnetic field localization. This allows the pillars 102 to be used for sensing plasmonic or surface enhanced Raman signals when irradiated. Other parts of the inner surface of the micro-fluidic channel 101, e.g., the surface in between the pillars 102, may also be configured for creating an electromagnetic field localization. Thus, the inner surface of the micro-fluidic channel 101 in between the pillars 102 and the side-walls of the inner micro-fluidic channel 101 may also be used for sensing purposes. This increases the surface area of the sensing region. As an advantage, the sensitivity of the sensing region is increased.

The pillars 102 are configured for creating a capillary action in the micro-fluidic channel 101 when a fluid is present in the micro-fluidic channel 101. The capillary action in the micro-fluidic channel 101 allows a fluid sample to propagate through the micro-fluidic channel 101 without the need of extra components such as a pump. This reduces the cost and size of the device, thereby enabling the device to be used as a disposable device.

According to an embodiment of the disclosure, the configuration of the plurality of pillars 102 for creating a capillary action comprises pillars each having a height, a diameter, and a spacing in between pillars 102 adapted for creating the capillary action in the micro-fluidic channel 101. The diameter of the pillars 102 may range from 1 nm to 1 mm. The aspect ratio (i.e., the height of a pillar divided by the diameter of that pillar) of the pillars 102 may range from 0.1 to 100. According to a specific embodiment, the height of a pillar is 25 um, the diameter of a pillar is 2 um and the distance between pillars 102 is 1 micrometer (μm). According to another embodiment, the height of a pillar is 25 um, the diameter of a pillar is 5 um and the distance between pillars 102 is 2.5 um. According to another embodiment, the height of a pillar is 25 um, the diameter of a pillar is 2.5 um and the distance between pillars 102 is 1.25 um. The plurality of pillars may be fabricated from silicon. The material silicon allows the pillars to be fabricated in a very dense way with very high aspect ratios. This increases the surface area of the sensing region. As an advantage, the sensing region has an increased sensitivity.

It is an advantage of the disclosure that the sensing region has double functionality. The sensing region is used to detect analytes in a fluid sample and at the same time used to propagate the fluid sample through the micro-fluidic device 100. This configuration allows the device to be very compact and cheap. For example, the micro-fluidic device 100 may be used as a disposable cartridge in an external device which comprises other components, e.g., a radiation source, a detector, a processing unit, to irradiate the micro-fluidic device 100 and to detect plasmon resonance or Raman scattering on/from the device.

FIG. 1 illustrates an embodiment of the first aspect of the disclosure. A plurality of pillars 102 is located in the micro-fluidic channel 101. The pillars 102 are positioned on an inner surface, for example on a bottom surface of the micro-fluidic channel 101.

Figure 2:
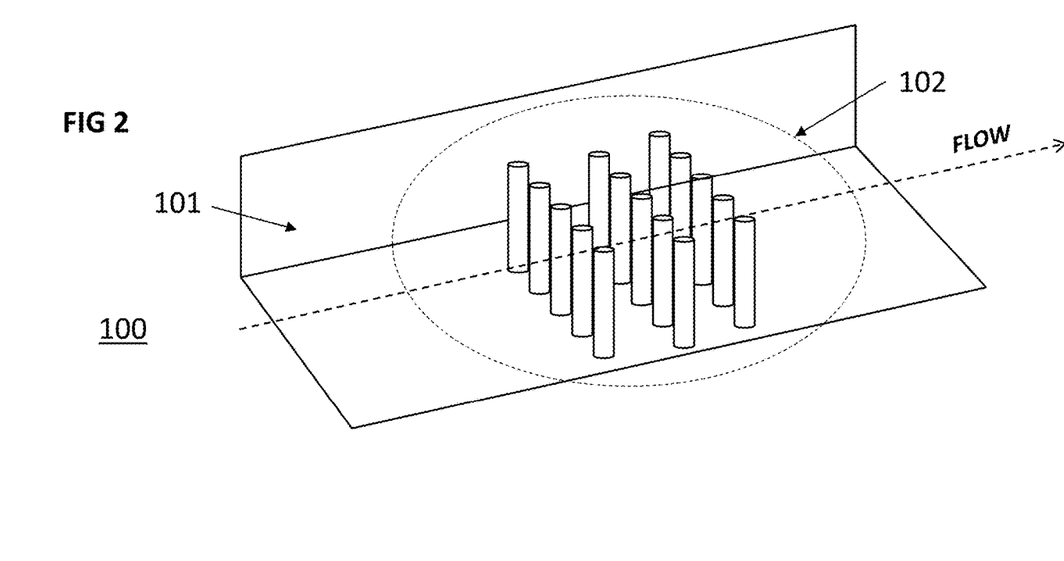
FIG. 2 illustrates a 3D view of an embodiment of the disclosure

FIG. 2 illustrates a 3D view of the inside of the micro-fluidic channel 101. The pillars 102 are configured for creating an electromagnetic field localization. Further, the number of pillars 102, the size of the pillars 102 and the distance between the pillars 102 is determined to create a capillary action in the micro-fluidic channel 101.

When a fluid sample is introduced in the micro-fluidic channel 101, due to the capillary action created by the pillars 102, the fluid sample will propagate through the micro-fluidic channel 101 without the need of any extra components. Due to the configuration of the sensing region, an analyte present in the fluid sample is adsorbed on the surface of the sensing region. When the sensing region is irradiated, surface plasmon resonance or Raman scattering may be measured using an external detector. The measurement of the surface plasmon resonance may be done e.g., by analyzing the LSPR spectrum peak wavelength or the LSPR spectrum peak intensity or by analyzing both. This can be done in transmission or reflection mode depending on the material used to fabricate the device: e.g., transparent or not transparent. The measurement of the Raman scattering may be done by measuring the intensity of the Raman signal representing the Raman scattering. The measurements may be correlated to the presence or the concentration of an analyte in the fluid sample.

Figure 6:
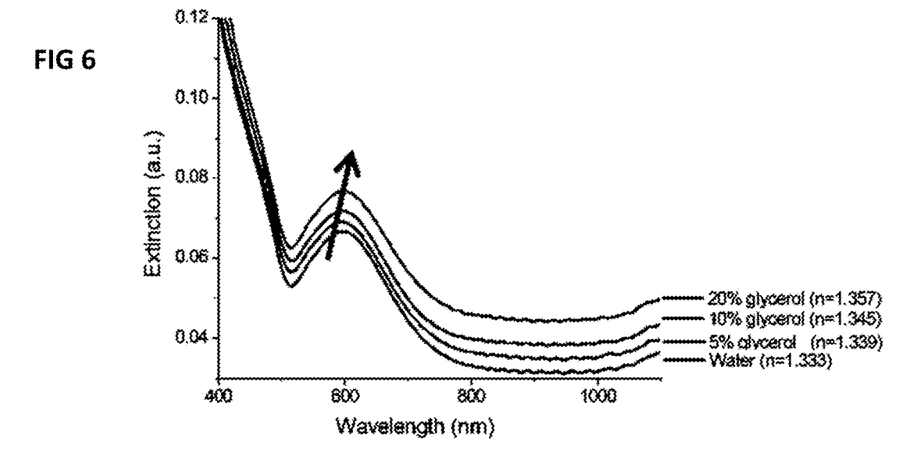

Experimental data of the detection of an analyte in a micro-fluidic device 100 according to the first aspect of the disclosure is illustrated in FIG. 6. To assess the sensitivity of the micro-fluidic device 100 to its environmental refractive index (RI) change, UV-visible spectroscopy (UV-vis) is used when droplets of various solutions with different RI were introduced into the device. Extinction spectra of the micro-fluidic device 100 when various solutions with different RI were introduced into the micro-fluidic device 100 are illustrated. The various solutions comprise: a water sample, a fluid sample comprising 5%, 10% and 20% glycerol. A shift of the graphs for different analytes is noticeable.

Figure 7A:
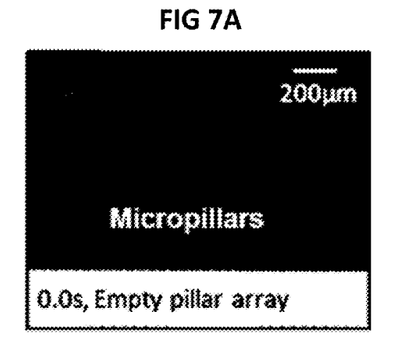
Figure 7B:
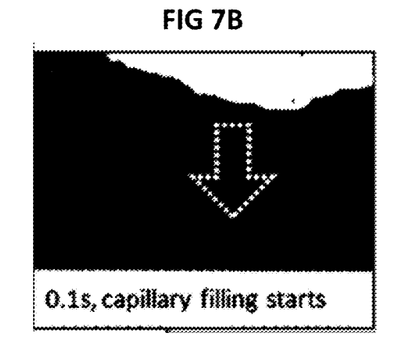
Figure 7C:
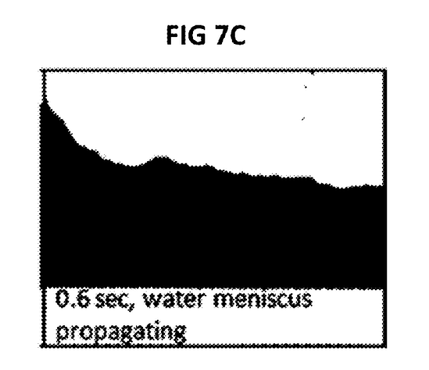
Figure 7D:
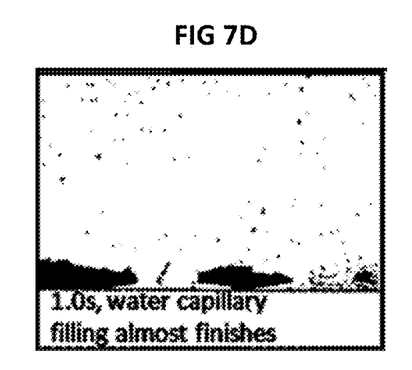

FIGS. 7A-D illustrate the capillary action created by the pillars 102 in the micro-fluidic channel 101. To characterize the capillary flow behavior of the micro-fluidic devices, liquid propagation was studied by adding a 20 μL droplet of water on one end of the micro-fluidic device 100. The water propagation along the channel was analyzed. The even distribution of the water through the micro-fluidic channel 101 is illustrated. This even distribution is advantageous as all the pillars 102 in the micro-fluidic channel 101 are contacted with the fluid sample resulting in a high sensitivity of analyte sensing. FIG. 7A illustrates a top view of an empty micro-fluidic channel 101 with pillars 102. FIG. 7B illustrates a top view of a micro-fluidic channel 101 with pillars 102 when a fluid sample was present in the micro-fluidic channel 101 for 0.1 seconds. The white area corresponds to the part of the channel filled with the fluid sample. FIG. 7C illustrates a top view of a micro-fluidic channel 101 with pillars 102 when a fluid sample was present in the micro-fluidic channel 101 for 0.6 seconds. FIG. 7D illustrates a top view of a micro-fluidic channel 101 with pillars 102 when a fluid sample was present in the micro-fluidic channel 101 for 1 second.

According to an embodiment of the disclosure, the configuration of the sensing region for adsorbing an analyte comprises a surface chemistry layer for binding an analyte. The surface chemistry may comprise a bioreceptor such as an antibody or a DNA probe to capture the analyte from the fluid sample.

According to an embodiment of the disclosure, the surface chemistry layer does not bind labeled analytes. For example, an analyte with a fluorescent label will not bind to the surface chemistry layer.

According to an embodiment of the disclosure, the configuration of the sensing region for adsorbing an analyte comprises a surface chemistry layer with multiple regions wherein each region comprises a different bioreceptor for binding different analytes. Multiple regions may be created by using different masks wherein different masks are used for depositing different surface chemistry layers on the sensing region.

The sensing region may comprise multiple sub-regions functionalized with different bioreceptors. The different bioreceptors bind different analytes. This allows a micro-fluidic device 100 to detect different analytes. The surface chemistry layer is located on the sensing region to adsorb selected analytes on the sensing region. The surface chemistry layer may be located on the sensing region and on other or all inner surfaces of the micro-fluidic channel 101. Thus, all inner surfaces of the micro-fluidic channel 101, including the surfaces of the pillars, may be used as a sensing region.

As LSPR or SERS are label-free detection techniques, attaching a label such as a fluorescent label to the analyte prior to providing the fluid sample in the device 100 is not required. This would complicate the use and manufacturability of the device. It is advantageous as complex and time consuming additional preparation steps on a fluid sample are not required. It is a further advantage that the device can be used outside of a lab environment. For example, a body fluid (e.g., a blood sample) from a user can be directly provided in the device 100 without any intervention or extra preparation steps on the fluid sample. Hence, a real-time detection of analytes in the fluid sample is possible.

Figure 3:
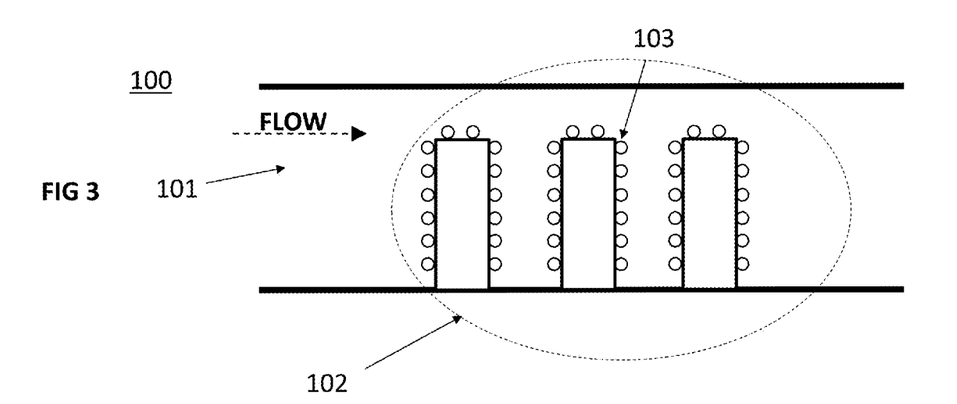
FIG. 3 illustrates an embodiment of the disclosure comprising nanoparticles or nanostructures

According to an embodiment of the disclosure, the configuration of the plurality of pillars 102 for creating an electromagnetic field localization comprises plasmonic nanoparticles or plasmonic nanostructures 103 located on the surface of the plurality of pillars 102.

Figure 5:
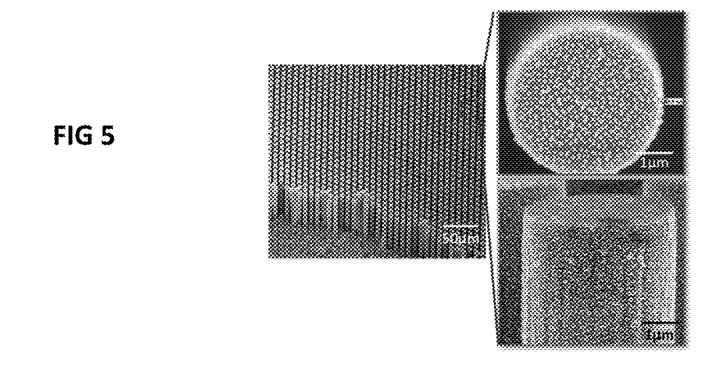
FIG. 5 illustrates SEM images of pillars comprising nanoparticles FIG. 6 illustrate LSPR spectra of different analytes FIG. 7 A-D illustrates the capillary action in a micro-fluidic channel created by pillars after 0 s, 0.1 s, 0.6 s and 1 s.

Plasmonic nanoparticles or plasmonic nanostructures are nanoparticles or nanostructures fabricated from a plasmonic material and suitable for performing LSPR or SERS. After a chemical surface modification of the pillars, the nanostructures or nanoparticles are deposited on the pillars. FIG. 5 illustrates SEM images of high-aspect Silicon pillars comprising nanoparticles at the surface of the pillars. An even distribution of the nanoparticles on the pillars is noticeable.

According to embodiments of the disclosure, the nanostructures may be nanospheres, nanorods, branched nanoparticles, nanocore-shell structures or any other structure suitable for performing LSPR or SERS techniques.

The nanoparticles or nanostructures 103 allow the use of LSPR and SERS to detect analytes. When a fluid sample containing an analyte is introduced in the micro-fluidic device 100, the analyte is adsorbed on the surface of the nanoparticles or nanostructures 103. The analyte may be detected by e.g., measuring a surface plasmon resonance or measuring Raman scattering from the nanoparticles or nanostructures 103 when irradiated. The nanoparticles or nanostructures 103 may be fabricated from gold, silver or copper or any other suitable material for performing LSPR or SERS. The material of the nanoparticles or nanostructures 103 may be gold, silver or copper or any other suitable material for performing LSPR or SERS.

The nanoparticles or nanostructures 103 may comprise a surface chemistry layer configured for adsorbing a specific analyte on their surface. The surface chemistry layer may be a layer which binds a label-free analyte. The surface chemistry layer may be a layer which does not bind a labeled analyte. The surface chemistry layer may e.g., be a silane layer configured with receptors, e.g., bioreceptors, for binding a specific analyte.

According to an embodiment of the disclosure, the configuration of the plurality of pillars 103 for creating an electromagnetic field localization comprises the plurality of pillars 102 being fabricated from a plasmonic material. The surface roughness of the plurality of pillars 102 is suitable for performing LSPR or SERS.

The pillars 102 may be completely fabricated from gold, silver, copper or any other material suitable for performing LSPR or SERS techniques. The material of the pillars 102 may be gold, silver, copper, or any other material suitable for performing LSPR or SERS techniques. The roughness of the surface of the pillars is adapted to create an electromagnetic field localization, allowing LSPR and SERS techniques to detect analytes adsorbed on the surface of the pillars.

The material of the pillars 102 and the roughness of the surface of the pillars 102 are selected to feature surface plasmon resonance or Raman scattering when analytes are adsorbed on the pillars and when the pillars are irradiated with a radiation source configured for exciting surface plasmons. The pillars may be fabricated using an etching technique that etches the pillars 102 and automatically creates the desired roughness of the pillars depending on the type of etching.

Pillars which are fabricated from a plasmonic material may be further referred to in this disclosure as "plasmonic pillars."

The surface of the plasmonic pillars 203 may comprise a surface chemistry layer for adsorbing an analyte on the surface of the plasmonic pillars. The surface chemistry layer may be a layer which binds label-free analytes. The surface chemistry layer may be a layer which does not bind labeled analytes.

Figure 4:
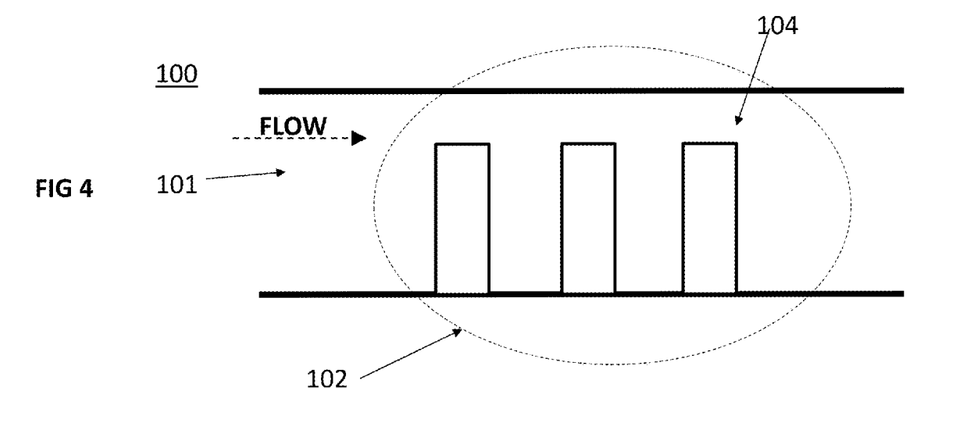
FIG. 4 illustrates an embodiment of the disclosure comprising a plasmonic coating

According to an embodiment of the disclosure, the configuration of the plurality of pillars 102 for creating an electromagnetic field localization comprises the plurality of pillars 102 having a coating 104 with a plasmonic material. The surface roughness of the coating is suitable for performing LSPR or SERS.

The pillars may be coated with a thin metal film which gives rise to surface plasmon resonance or Raman scattering when selected analytes are adsorbed on the surface of the pillars and when the thin film is irradiated with a radiation source configured for exciting surface plasmons. The thin film may be a gold, silver or copper layer or any other material suitable for performing LSPR and SERS. The thin film may comprise a surface chemistry layer for binding selected analytes. This surface chemistry layer may be a layer which binds label-free analytes. This surface chemistry layer may be a layer which does not bind labeled analytes.

According to an embodiment of the disclosure, inner surfaces of the micro-fluidic channel 101 and/or the plurality of pillars 102 comprise a hydrophilic layer and/or a hydrophobic layer.

The hydrophobic layer ensures a large contact angle between a fluid sample and the inner surface of the micro-fluidic channel 101. As an advantage the hydrophobic layer eases the propagation of the fluid sample through the micro-fluidic channel 101. As another advantage, a hydrophobic layer may be used to change the propagation speed of a fluid sample in the micro-fluidic channel 101 in certain regions. The hydrophilic layer ensures a small contact angle between a fluid sample and inner surfaces of the micro-fluidic channel. This may be advantageous to e.g., change the propagation speed of a fluid sample in the micro-fluidic channel 101.

According to an embodiment of the disclosure, a region of the micro-fluidic channel 101 without pillars comprises a hydrophobic layer on one surface and a hydrophilic layer on the opposite surface. According to an embodiment of the disclosure, an area of the inner surface of the micro-fluidic channel 101 outside the sensing region comprises a hydrophobic layer while an area of the inner surface opposite to this hydrophobic layer comprises a hydrophilic layer.

A hydrophilic layer on an inner surface of the micro-fluidic channel 101 facing a hydrophobic layer on an inner surface of the micro-fluidic channel may be used to allow a fluid sample to propagate through regions of the micro-fluidic channel 101 without pillars 102. Thus, the combination of a hydrophobic layer opposing a hydrophilic layer may be used to bridge a gap or a region in the micro-fluidic channel 102 without pillars.

According to an embodiment of the disclosure, the micro-fluidic channel 101 and the plurality of pillars 102 are fabricated from silicon. The micro-fluidic channel 101 may be etched in a single piece of silicon wherein the plurality of pillars 102 are fabricated while etching the micro-fluidic channel 102. It is an advantage to use silicon rather than more common microfluidic materials such as glass or polymers since the very high anisotropic etching of silicon results in fine structures with extremely high aspect ratios. As an advantage, high aspect ratio of pillars 102 increases the area of the sensing region. The silicon micro-pillars 102 typically have lateral dimensions from 1 um to 20 um with aspect ratios of 20-50. High aspect ratios are advantageous in having a high surface to volume ratio; essential for capillary flow. Moreover, silicon is an inert material with clear advantages towards implementation of biochemical reactions. Finally, one or more micro-fluidic channels can be combined on one silicon chip allowing multiplexed detection of one analyte spread over different channels or for multi-analyte detection on one chip.

According to an embodiment of the disclosure, the micro-fluidic channel 101 and the plurality of pillars 102 are fully or partly fabricated from an optical transparent material. For example, the transparent material may be glass or a polymer. The transparent material allows light to propagate through the micro-fluidic device. As an advantage, detection may be done in transmission mode instead of in reflection mode. As another advantage, optical inspection tools may be used to inspect the inside of the micro-fluidic channel 102.

Figure 8:
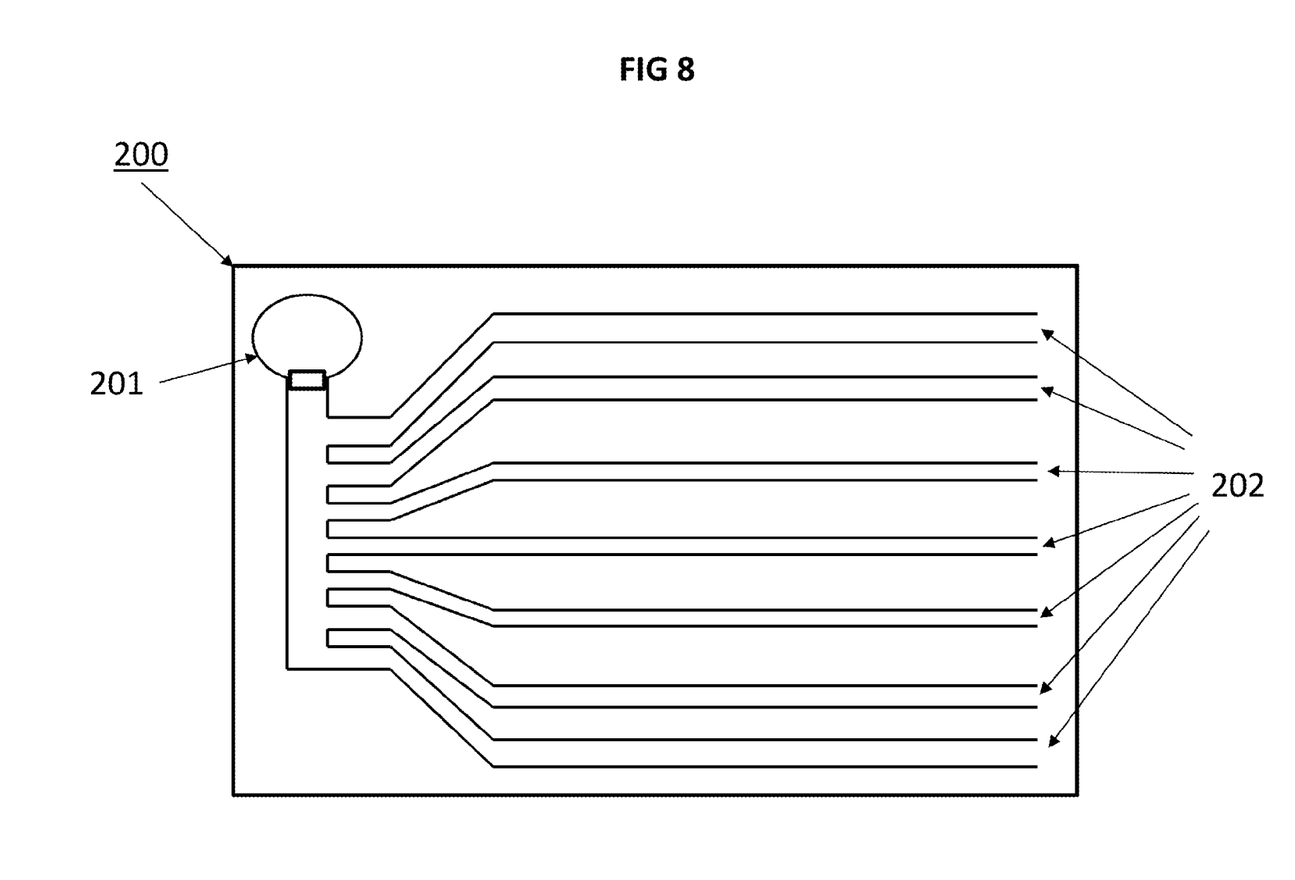
FIG. 8 illustrates a micro-chip with multiple micro-fluidic channels for the detection of analytes in a fluid sample according to an embodiment

In a second aspect of the disclosure, a multiplexed plasmonic microchip for detecting at least one analyte in a fluid sample is presented. Such a micro-chip is illustrated in FIG. 8. The system comprises a plurality of micro-fluidic devices 202 as presented in the first aspect of the disclosure and a supply system for providing the fluid sample to the plurality of micro-fluidic devices 201.

The multiplexed plasmonic micro-chip 200 may comprise a substrate 208 wherein a plurality of micro-fluidic devices 202, as described in the first aspect of the disclosure, are embedded. The substrate 208 may be a silicon substrate. A fluid sample can be provided in each micro-fluidic device 202 through the supply system for providing the fluid sample to the plurality of micro-fluidic devices which is fluidically connected to each micro-fluidic device 202. This allows the fluid sample to be distributed among the plurality of micro-fluidic devices 202 and allows a multiplexed detection of analytes in a fluid sample. As an advantage, a faster and more sensitive detection can be done. When using multiple micro-fluidic devices 202, a larger volume of the fluid sample can be analyzed. As an advantage, more precise concentration measurements of an analyte in a fluid sample can be achieved.

Figure 9:
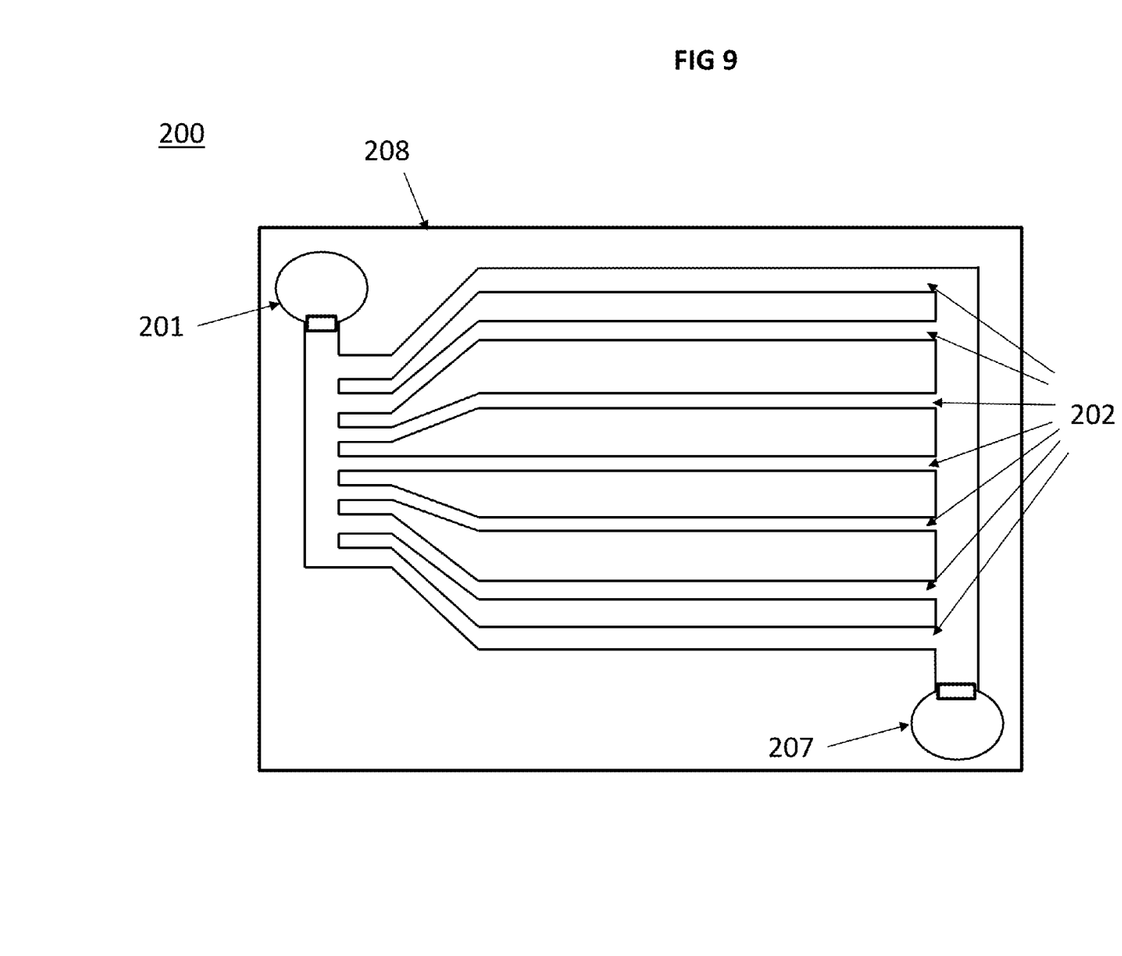
FIG. 9 illustrates a micro-chip with multiple micro-fluidic channels for the detection of analytes in a fluid sample according to an embodiment

According to an embodiment of the disclosure, the multiplexed plasmonic microchip 200 may further comprise an outlet 207 fluidically connected to the plurality of micro-fluidic device 202. The outlet 207 may be used for exiting a fluid sample from the multiplexed plasmonic microchip 200 after propagation through each micro-fluidic device. As an advantage, the multiplexed plasmonic microchip 200 may be used to continuously detect analytes in provided fluid samples. This is illustrated in FIG. 9.

According to an embodiment of the disclosure, different micro-fluidic devices 202 are configured for adsorbing different analytes.

The sensing region of each micro-fluidic device is configured for adsorbing an analyte to its surface. Sensing regions of different micro-fluidic devices 202 may be configured for adsorbing different analytes. For example, the sensing region of a first micro-fluidic device may be configured to adsorb analyte A while the sensing region of a second micro-fluidic device may be configured to adsorb analyte B. This difference in configuration allows a multiplexed detection of analyte A and analyte B. Thus, different analytes may be detected simultaneously. Different sensing regions may be fabricated by using different masks.

The fabrication of the multiplexed plasmonic microchip 200 may be done using standard lithographic techniques allowing a very dense occupation of different micro-fluidic devices 202 on the microchip resulting in a very compact sensing device for performing multiplexed analysis.

The multiplexed plasmonic microchip 200 may further comprise a transistor layer. The transistor layer may be used to electrically connect other electronic components located on the microchip 200. The transistor layer may be a CMOS layer.

Figure 10:
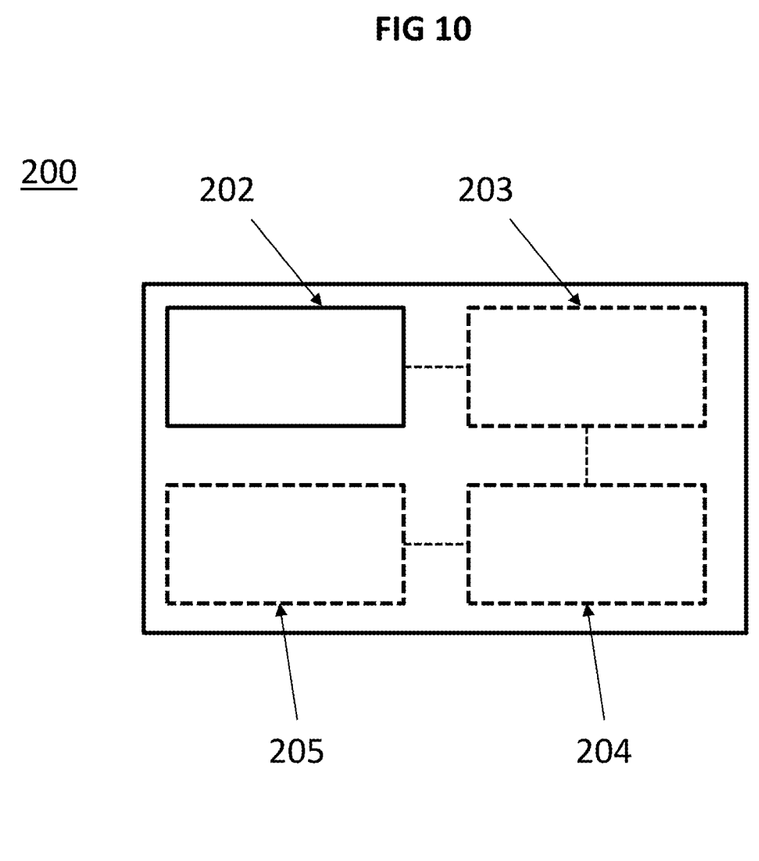
FIG. 10 illustrates a block diagram of a multiplexed plasmonic microchip according to an embodiment

The multiplexed plasmonic microchip 200 may further comprise a measurement unit 203 for measuring surface plasmon resonance or Raman scattering from the plurality of micro-fluidic devices 202. The measurement unit 203 may be integrated in the multiplexed plasmonic microchip 200 and electrically connected to a transistor layer present in the multiplexed plasmonic microchip 200. The multiplexed plasmonic microchip 200 may further comprise a computing unit 204 for correlating the measured surface plasmon resonance or Raman scattering to the presence or concentration of the analyte in the fluid sample. The computing unit 204 may be, e.g., a central processing unit. The computing unit 204 may be integrated in the transistor layer or may be a separate component located on the micro-chip 200 and electrically connected to the transistor layer. The computing unit 204 may be connected to the measurement unit 203. The multiplexed plasmonic microchip 200 may further comprise a telecommunication unit 205 for transmitting data wirelessly to an external device. The telecommunication unit 205 may be integrated in the transistor layer or may be a separate component located on the micro-chip 200 and electrically connected to the transistor layer. The telecommunication unit 205 may be connected to the computing unit 204 for transmitting data computed by the computing unit 204. The telecommunication unit 205 may be connected to the measurement unit 203 for transmitting measurement data to an external device. Such an embodiment is illustrated in FIG. 10.

The multiplexed plasmonic microchip 200 may further comprise a radiation source for irradiating the plurality of micro-fluidic devices 202 and configured to excite surface plasmons. The radiation source may be a light source configured to emit a light beam suitable for performing LSRP or SERS. For example, the light source may be a laser. The laser may have a wavelength of 785 nm.

According to a third aspect of the disclosure, a method for detecting at least one analyte in a fluid sample is presented, using the device presented in the second aspect of the disclosure. The method comprises: providing a fluid sample in the plurality of micro-fluidic devices using the supply system for providing the fluid sample to the plurality of micro-fluidic devices (202); irradiating the plurality of micro-fluidic devices 202 with the fluid sample; measuring surface plasmonic resonance or Raman scattering from the plurality of irradiated micro-fluidic devices 202; and correlating the measured surface plasmonic resonance or Raman scattering to the presence or concentration of the at least one analyte in the fluid sample.

According to the first aspect, second and third aspect of the disclosure or according to any of its embodiments, the at least one analyte is a label-free analyte.

The micro-fluidic device as described in the first aspect of the disclosure may be fabricated by patterning a substrate to simultaneously create a plurality of pillars in a micro-fluidic channel. Thereafter, a solution may be propagated through the micro-fluidic channel thereby chemically treating the pillars to allow attachment of nanoparticles or nanostructures. Thereafter, a solution comprising such nanoparticles or nanostructures may be propagated through the micro-fluidic channel to attach nanoparticles or nanostructures to the pillars. Thereafter functionalization of the nanoparticles may be performed.

Alternatively, the micro-fluidic device as described in the first aspect of the disclosure may be fabricated by depositing a plasmonic material layer on a substrate. Thereafter, the plasmonic material layer is patterned to simultaneously create a plurality of pillars in a micro-fluidic channel in the plasmonic material layer. Thereafter functionalization of the pillars may be performed.

Alternatively, the micro-fluidic device as described in the first aspect of the disclosure may be fabricated by patterning a substrate to simultaneously create a plurality of pillars in a micro-fluidic channel. Thereafter, a thin plasmonic material layer may be deposited on the plurality of pillars. Thereafter functionalization of the pillars may be performed.

The multiplexed plasmonic microchip 200 as described in the second aspect of the disclosure may be fabricated using any of the techniques described above wherein a plurality of micro-fluidic devices are fabricated in a single substrate, e.g., a silicon substrate.

The invention claimed is:

1. A micro-fluidic device comprising:
   a micro-fluidic channel having an inner surface;
   a sensing region inside the micro-fluidic channel configured for adsorbing at least one analyte, the sensing region comprising a plurality of pillars positioned along the length of the inner surface of the micro-fluidic channel wherein the plurality of pillars are configured for creating an electromagnetic field localization thereby making the sensing region suitable for sensing plasmonic or surface enhanced Raman signals when irradiated;
   wherein,
   the plurality of pillars are further configured for creating a capillary action in the micro-fluidic channel when a fluid sample is present in the micro-fluidic channel.

2. The micro-fluidic device according to claim 1 wherein the sensing region is configured for adsorbing an analyte by containing a surface chemistry layer for binding at least one analyte.

3. The micro-fluidic device according to claim 1, wherein the plurality of pillars is configured for creating an electromagnetic field localization by having plasmonic nanoparticles or plasmonic nanostructures positioned on the surface of the plurality of pillars.

4. The micro-fluidic device according to claim 1, wherein the plurality of pillars is configured for creating an electromagnetic field localization by having the plurality of pillars fabricated from a plasmonic material.

5. The micro-fluidic device according to claim 1, wherein the plurality of pillars is configured for creating an electromagnetic field localization by having a coating of a plasmonic material.

6. The micro-fluidic device according to claim 1, wherein the plurality of pillars is configured for creating a capillary action by having each pillar having a height, a diameter, and a spacing in between each pillars adapted for creating the capillary action in the micro-fluidic channel.

7. The micro-fluidic device according to claim 1 wherein the micro-fluidic channel and the plurality of pillars are fabricated from silicon.

8. The micro-fluidic device according to claim 1 wherein the micro-fluidic channel and the plurality of pillars are at least partially fabricated from an optical transparent material.

9. A multiplexed plasmonic microchip for detecting at least one analyte in a fluid sample, the system comprising:
   a plurality of micro-fluidic devices according to claim 1;
   a supply system for providing the fluid sample to the plurality of micro-fluidic devices.

10. The multiplexed plasmonic microchip according to claim 9 wherein different micro-fluidic devices are configured for adsorbing different analytes.

11. The multiplexed plasmonic microchip according to claim 9, further comprising a transistor layer.

12. The micro-fluidic device according to claim 2, wherein the plurality of pillars is configured for creating a capillary action by having each pillar having a height, a diameter, and a spacing in between each pillars adapted for creating the capillary action in the micro-fluidic channel.

13. The micro-fluidic device according to claim 12 wherein the micro-fluidic channel and the plurality of pillars are fabricated from silicon.

14. The micro-fluidic device according to claim 13 wherein the micro-fluidic channel and the plurality of pillars are at least partially fabricated from an optical transparent material.

15. A method for detecting at least one analyte in a fluid sample, the method comprising:
   introducing a fluid sample to the multiplexed plasmonic microchip according to claim 9 by providing the fluid sample to the plurality of micro-fluidic devices using the supply system;
   irradiating the plurality of micro-fluidic devices and the fluid sample with a radiation source configured to perform LSPR or SERS;

measuring surface plasmon resonance or Raman scattering from the plurality of irradiated micro-fluidic devices; and correlating the measured surface plasmonic resonance or Raman scattering to the presence or concentration of the at least one analyte in the fluid sample.

16. The method according to claim 15 wherein the at least one analyte is a label-free analyte.

17. The method according to claim 15, wherein the different micro-fluidic devices are configured for adsorbing different analytes.

18. The method according to claim 17, wherein the multiplexed plasmonic microchip further comprises a transistor layer.

* * * * *